US011061000B2

(12) United States Patent
Mihajlovic et al.

(10) Patent No.: US 11,061,000 B2
(45) Date of Patent: Jul. 13, 2021

(54) CMUT PROBE, SYSTEM AND METHOD

(71) Applicant: KONINKLIJKE PHILIPS N.V., Eindhoven (NL)

(72) Inventors: Nenad Mihajlovic, Eindhoven (NL); Antonia Cornelia van Rens, Nuenen (NL); Sergei Shulepov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 91 days.

(21) Appl. No.: 16/464,746

(22) PCT Filed: Nov. 30, 2017

(86) PCT No.: PCT/EP2017/080890
§ 371 (c)(1),
(2) Date: May 29, 2019

(87) PCT Pub. No.: WO2018/100015
PCT Pub. Date: Jun. 7, 2018

(65) Prior Publication Data
US 2019/0310231 A1 Oct. 10, 2019

(30) Foreign Application Priority Data
Dec. 1, 2016 (EP) .................................... 16201726

(51) Int. Cl.
*G01N 29/24* (2006.01)
*A61B 8/00* (2006.01)
(Continued)

(52) U.S. Cl.
CPC ....... *G01N 29/2406* (2013.01); *A61B 8/4272* (2013.01); *A61B 8/4438* (2013.01);
(Continued)

(58) Field of Classification Search
CPC ............... G01N 29/2406; G01N 29/30; G01N 2291/106; B06B 1/0292; B06B 1/0215;
(Continued)

(56) References Cited

U.S. PATENT DOCUMENTS 8,004,373 B2    8/2011   Huang
2005/0219953 A1* 10/2005  Bayram ................ B06B 1/0292
                                            367/178
(Continued)

FOREIGN PATENT DOCUMENTS

EP      2223654 A1      9/2010
WO      2015028945 A2   3/2015
WO      2016058963 A1   4/2016
WO      2016139087 A1   9/2016

OTHER PUBLICATIONS

International Search Report and Written Opinion for International Application No. PCT/EP2017/080890 filed Nov. 30, 2017, 15 pages.

*Primary Examiner* — Helen C Kwok

(57) ABSTRACT

Disclosed is an ultrasound probe that includes an array of CMUT (capacitive micromachined ultrasound transducer) cells. Each cell includes a substrate carrying a first electrode of an electrode arrangement. The substrate is spatially separated from a flexible membrane by a gap. The flexible membrane includes a second electrode of the electrode arrangement. The ultrasound probe also includes an acoustic window over the array of CMUT cells. The ultrasound probe further includes a data storage element accessible to an external control module of the ultrasound probe. The data storage element stores configuration information for configuring an operation of the array of CMUT cells in pre-collapse or collapse mode with the external control module to optimize the effective bandwidth of the array. Also disclosed is a calibration method of the ultrasound probe, an (Continued)

ultrasound system and a method of operating the ultrasound system.

15 Claims, 12 Drawing Sheets

(51) Int. Cl.
  *B06B 1/02* (2006.01)
  *G01N 29/30* (2006.01)
  *G01S 15/89* (2006.01)
  *G01S 7/52* (2006.01)
  *A61B 8/08* (2006.01)
  *G10K 11/32* (2006.01)

(52) U.S. Cl.
  CPC ............ *A61B 8/4494* (2013.01); *A61B 8/488* (2013.01); *A61B 8/58* (2013.01); *B06B 1/0215* (2013.01); *B06B 1/0292* (2013.01); *G01N 29/30* (2013.01); *G01S 7/5208* (2013.01); *G01S 15/8915* (2013.01); *G01S 15/8954* (2013.01); *A61B 8/466* (2013.01); *A61B 8/523* (2013.01); *B06B 2201/51* (2013.01); *G01N 2291/106* (2013.01); *G10K 11/32* (2013.01)

(58) Field of Classification Search
  CPC ... A61B 8/4272; A61B 8/4438; A61B 8/4494; A61B 8/488; A61B 8/58
  See application file for complete search history.

(56) References Cited

U.S. PATENT DOCUMENTS

| | | | |
|---|---|---|---|
| 2006/0116585 A1* | 6/2006 | Nguyen-Dinh | B06B 1/0292 600/459 |
| 2010/0173437 A1* | 7/2010 | Wygant | B06B 1/0292 438/53 |
| 2010/0312119 A1* | 12/2010 | Hashiba | B06B 1/0292 600/459 |
| 2011/0068654 A1* | 3/2011 | Cheng | B06B 1/0292 310/300 |
| 2011/0208059 A1 | 8/2011 | Cerofolini | |
| 2012/0010538 A1 | 1/2012 | Dirksen | |
| 2012/0104898 A1* | 5/2012 | Qu | H04R 19/005 310/319 |
| 2012/0112603 A1* | 5/2012 | Masaki | B81C 1/00047 310/308 |
| 2012/0133005 A1* | 5/2012 | Langeries | B06B 1/0292 257/416 |
| 2012/0194107 A1* | 8/2012 | Kandori | B06B 1/0246 318/116 |
| 2013/0116568 A1* | 5/2013 | Certon | A61B 8/145 600/447 |
| 2014/0117809 A1* | 5/2014 | Zemp | B06B 1/0292 310/308 |
| 2014/0247698 A1* | 9/2014 | Dirksen | H04R 31/00 367/189 |
| 2014/0265728 A1* | 9/2014 | Li | G01N 29/06 310/321 |
| 2016/0158580 A1 | 6/2016 | Slayton et al. | |
| 2016/0203809 A1 | 7/2016 | Brock-Fisher et al. | |

* cited by examiner

US 11,061,000 B2

CMUT PROBE, SYSTEM AND METHOD

RELATED APPLICATION

This application is the U.S. National Phase application under 35 U.S.C. § 371 of International Application No. PCT/EP2017/080890, filed on Nov. 30, 2017, which claims the benefit of European Application No. EP16201726.3, filed Dec. 1, 2016. These applications are hereby incorporated by reference herein.

FIELD OF THE INVENTION

The present invention relates to an ultrasound probe or a patch (such as low profile ultrasound probe) including an array of CMUT cells, each cell comprising a substrate carrying a first electrode of an electrode arrangement, the substrate being spatially separated from a flexible membrane including a second electrode of said electrode arrangement by a gap and an acoustic window over the array of CMUT cells.

The present invention further relates to an ultrasound or monitoring system comprising such an ultrasound probe.

The present invention yet further relates to a method of calibrating such an ultrasound probe.

The present invention still further relates to a method of operating such an ultrasound system.

BACKGROUND OF THE INVENTION

Ultrasonic transducers used for medical imaging have numerous characteristics that lead to the production of high quality diagnostic images. Among these are broad bandwidth, affecting resolution and high sensitivity, which combined with pressure output affects depth of field of acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks. Firstly, the ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements. Moreover, PZT materials have poorly matched impedance to water or biological tissue, such that a set of matching layers needs to be added to the PZT materials in order to obtain the desired acoustic impedance matching with the medium of interest.

As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, e.g. probes, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems.

The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the Capacitive MUT (CMUT). CMUT transducers are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUTs can be connected together and operated in unison as a single transducer element. For example, four to sixteen CMUTs can be coupled together to function in unison as a single transducer element. A typical 2D transducer array can have 2,000-10,000 CMUT transducer elements by way of example.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which yields an improved effective bandwidth and relaxes the requirements on the acoustic windows compared to, e.g. because fewer material layers are required in such acoustic windows. EP 2 223 654 A1 discloses an ultrasonic diagnostic apparatus having an ultrasonic probe comprising plural vibrating elements whose electromagnetic coupling coefficients vary in accordance with the magnitude of a bias voltage supplied from a bias voltage unit. The ultrasonic probe contains a memory in which information concerning the ultrasonic probe such as bias voltage may be stored to prevent collapse of the vibrating elements during operation of the ultrasonic probe.

However, the bandwidth of such CMUTs may be further improved by operating them in so-called collapse mode, in which part of the CMUT membrane is forced (collapsed) onto the opposing substrate by applying a large enough bias voltage across the electrodes of the CMUT. However, the effective bandwidth that can be achieved may be limited by the material(s) used in the acoustic window. Typically, the acoustic window should be soft enough such that it does not prevent CMUT membranes from movement whilst at the same time provide mechanical protection, be biocompatible and have an acoustic impedance close to that of tissue (about 1.6 MRayl) and/or have a thickness that is small compared to the wavelength of the ultrasound waves generated with the CMUT. Meeting all these requirements often proves to be practically impossible, such that in practice materials, e.g. polymers, are chosen that have good flexibility and mechanical characteristics but may not have optimal acoustic impedance, and may not be biocompatible, in which case a thin biocompatible (polymer) layer may be deployed over the main layer of the acoustic window. An example of a CMUT cell having such an acoustic window is disclosed in US 2016/0203809 A1.

However, such cells typically exhibit an acoustic impedance mismatch (typically a lower acoustic impedance) with respect to tissue at the vibrating part of the membrane. If the layer of the acoustic window contacting CMUT membrane, e.g. a single layer acoustic window or the inner layer of a multi-layered acoustic window, is such that its acoustic impedance is smaller than impedance of the outer propagation medium (typical acoustic impedance of tissue is 1.6 MRayls), this causes the pulse echoes collected with such CMUTs to exhibit resonance peaks at frequencies $f=(2k-1)(C_M/4d_M)$, in which k is a positive integer (with k defining the kth order resonance), $C_M$ is the speed of sound through acoustic window material M and $d_M$ is the thickness of the acoustic window material M. Similarly, if this layer has an acoustic impedance higher than the acoustic impedance of the propagation medium (e.g. higher than 1.6 MRayls), the resonance peaks will occur at frequencies $f=(k+1)(C_M/2d_M)$.

Therefore, there exists a need to minimize the impact of such acoustic window resonances in the pulse echoes collected with such CMUTs in order to improve their effective bandwidth characteristics.

SUMMARY OF THE INVENTION

The present invention seeks to provide an ultrasound probe or a patch comprising an array of CMUTs and an acoustic window over the CMUTs that may be operated with a high effective bandwidth.

The present invention further seeks to provide an ultrasound system comprising such an ultrasound probe.

The present invention yet further seeks to provide a method of calibrating such an ultrasound probe.

The present invention still further seeks to provide a method of operating such an ultrasound system.

In accordance with a first aspect, there is provided an ultrasound probe or a patch (such as low profile ultrasound probe) including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap; an acoustic window over the array of CMUT cells; and a data storage element accessible to an external control module of the ultrasound probe, the data storage element storing configuration information for configuring an operation of the array of CMUT cells with the external control module, said configuration information causing the operation of each CMUT cell in collapse mode or pre-collapse mode in which a configurable area of the flexible membrane is collapsed onto the substrate; and causing the generation of a composite resonance spectrum during operation of said CMUT cells that includes a resonance spectrum of the CMUT cells and a first order resonance frequency of the acoustic window at least partially overlapped by the resonance spectrum of the CMUT cells, wherein a region of said composite resonance spectrum delimited by a peak resonance frequency of the CMUT cells and said first order resonance frequency exhibits a minimum resonance strength no more than 6 dB below the maximal resonance strength of the composite resonance spectrum (as determined from a received pulse echo) or said peak resonance frequency coincides with the first order resonance frequency in order to optimize the effective bandwidth of the array.

The present invention is based on the insight that the effective bandwidth or power spectrum of (the pulse echoes of) CMUT cells is a function of the operating parameters of such CMUT cells, which particularly is true when the CMUT cells are operated in a pre-collapse or collapse mode, for which it is well-known per se that CMUT cells operated in such modes as the center or peak resonance frequency of the cells may be controlled, i.e. tuned, by operating parameters including the bias voltage applied to such cells, which determines the area of the CMUT membrane that is collapsed onto the opposite substrate. This may be utilized to optimize the power spectrum of the pulse echoes of such CMUT cells by pre-configuring one or more operating parameters such as the bias voltage.

Obtaining such operating parameters is a non-trivial exercise that is beyond many medical practitioners operating such ultrasound probes (patches). Moreover, in order to be able to obtain such operating parameters in a time-efficient manner, a priori knowledge about the effective thickness of the CMUT membranes and the acoustic window deployed thereon is required such that the CMUT array may be efficiently calibrated to obtain the appropriate operating parameters such as the bias voltage at which the CMUT cells should be operated. Hence, this is ideally performed at the manufacturing site of such an ultrasound probe. Therefore, the provisioning of a data storage element including such operating parameters as part of the ultrasound probe facilitates the storage of the appropriate operating parameters in the data storage element at the site of manufacture whilst the ultrasound probe may be operated in its optimized configuration at the point of care, e.g. by a medical practitioner, by an external control module of the ultrasound probe to which the probe is attached by simply retrieving the operating parameters from the data storage element and configuring itself in accordance with the retrieved operating parameters. When the ultrasound probe is operated in this manner, a particularly broad effective bandwidth is achieved. Specifically, where the configuration information is for aligning the peak resonance frequency of the CMUT cells with the first order resonance frequency of the acoustic window, the effective bandwidth of the CMUT cells may be maximized.

The data storage element may be any suitable element that can be machine-read. For example, the data storage element may be a barcode, QR (Quick Response) code or the like that may be read by an optical reader of the control module although in preferred embodiments the data storage element is a data storage device, e.g. a programmable data storage device such as an EEPROM or the like that may be read by the control module without the need for such an optical reader. Other programmable memory devices in which data may be retained in the absence of a power supply may equally be contemplated.

The configuration information may comprise a bias voltage specification for the CMUT cells to configure the effective bandwidth of the CMUT cells. For example, the configuration information may include the bias voltage at which the CMUT cells should be operated to ensure that the center resonance frequency of the CMUT cells in such a collapse mode or pre-collapse mode aligns with the resonance frequency of the acoustic window.

In an embodiment, the ultrasound probe further comprises a cable including a plug for connecting the ultrasound probe to the control module, wherein the data storage device is located in said plug. This for example is particularly advantageous in embodiments where the form factor of the ultrasound probe makes it difficult to integrate the data storage device within the probe housing, such as for example in embodiments wherein the ultrasound probe is comprised in a catheter or the like.

The acoustic window of the ultrasound probe may have any suitable composition. Typically, the acoustic window comprises a first polymer layer contacting the CMUT cells, which first polymer has suitable flexibility and mechanical properties, as well as a suitable acoustic impedance. In a preferred embodiment, the first polymer layer comprises PDMS. The first polymer layer may further comprise a filler material, e.g. filler particles, to tune the acoustic impedance of the first polymer.

The acoustic window may further comprise a second polymer layer over the first polymer layer, for example to make the acoustic window biocompatible and/or fluid-tight, i.e. water-tight. For example, the second polymer layer may comprise a polyether block amide (PEBAX) or parylene for this purpose. The thickness of the second polymer layer, if present, and if it is not well acoustically matched with tissue, is typically much smaller than the wavelength of the acoustic wave in the material. For example, the thickness of the second polymer layer may be 10% or less than the wavelength of an acoustic wave generated by the CMUT cells when travelling through the second polymer.

According to another aspect, there is provided an ultrasound system comprising the ultrasound probe of any of the herein described embodiments and a control module communicatively coupled to the ultrasound probe, wherein the control module is adapted to retrieve the configuration information from the data storage element; and operate the transducer array in accordance with the retrieved configuration information. Such an ultrasound system, e.g. a diagnostic imaging system or an interventional system, therefore benefits from automatically operating under optimized operating conditions (in terms of effective bandwidth of the CMUT array), thereby significantly improving its ease-of-use.

According to yet another aspect, there is provided a method of calibrating an ultrasound probe comprising an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap and being operable in a collapse mode in which a configurable area of the flexible membrane is collapsed onto the substrate; an acoustic window over the array of CMUT cells; and a data storage element accessible to a control module of the ultrasound probe, the method comprising systematically varying a set of operating parameters including a bias voltage of the CMUT cells; for each set of operating parameters, determining a composite resonance spectrum during operation of said CMUT cells that includes a resonance spectrum of the CMUT cells and a first order resonance frequency of the acoustic window at least partially overlapped by the resonance spectrum of the CMUT cells; determining the set of operating parameters causing a region of said composite resonance spectrum delimited by a peak resonance frequency of the CMUT cells and said first order resonance frequency to exhibit a minimum resonance strength no more than 6 dB below the maximum resonance strength of the composite resonance spectrum; or causing said peak resonance frequency to coincide with the first order resonance frequency (i.e. causing the largest effective bandwidth of the transducer array); and storing the determined set of operating parameters as configuration information in the data storage element. This calibration method facilitates automated optimal operation of the ultrasound probe in terms of effective bandwidth, thereby improving the ease of use of such an ultrasound probe.

In an embodiment, storing the determined set of operating parameters as configuration information in the data storage device further comprises storing an effective bandwidth of the transducer array achieved with the determined set of operating parameters in the data storage element. This for example facilitates a check at the point of care to determine whether the operating parameters stored in the ultrasound probe still cause the ultrasound probe to perform optimally, such that an end-user may manually adjust the operating parameters if this is no longer the case.

According to still another aspect, there is provided a method of operating the ultrasound system according to any of the embodiments described herein, the method comprising retrieving the configuration information from the data storage element with the control module; and operating the transducer array with the control module in accordance with the retrieved configuration information. This method ensures that the ultrasound system may operate under optimal operating conditions without requiring user intervention at the point of care.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
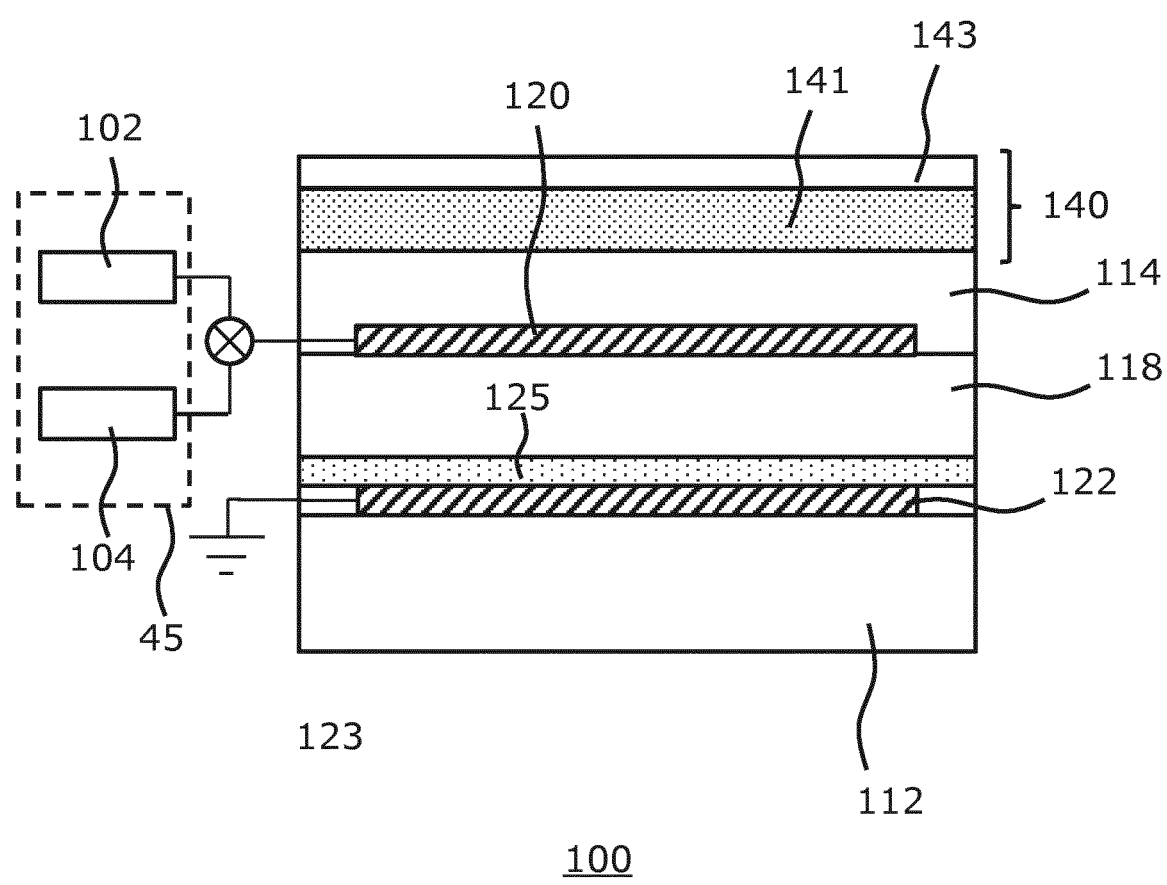
FIG. 1 schematically depicts an aspect of an ultrasound probe according to an embodiment.

It should be understood that the Figures are merely schematic and are not drawn to scale. It should also be understood that the same reference numerals are used throughout the Figures to indicate the same or similar parts.

FIG. 1 shows an aspect of an ultrasound probe or a patch such as low profile ultrasound probe 10 having a transducer array comprising CMUT cells 100. It shall be understood in the context of this description that the term ultrasound probe also includes low profile ultrasound probes such as patches suitable to be applied to skin of the patient. The application of the patches may be beneficial in ultrasound based monitoring for a longer period of time. As will be explained in further detail below, such an ultrasound probe may form part of an ultrasound diagnostic imaging or monitoring system in some embodiments or may form part of an ultrasound imaging-supported interventional system in some other embodiments. The present invention is not limited to a particular type of CMUT cells such that any suitable design of CMUT cell 100 may be contemplated. Such a CMUT cell 100 typically comprises a membrane or diaphragm 114 suspended above a silicon substrate 112 with a gap or cavity 118 there between. A top electrode 120 is located on the diaphragm 114 and moves with the diaphragm. A bottom electrode 122 is located on the floor of the cell on the upper surface of the substrate 112 in this example. Other realizations of the electrode 120 design can be considered, such as electrode 120 may be embedded in the membrane 114 or it may be deposited on the membrane 114 as an additional layer.

In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 112 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 1 the bottom electrode 122 is grounded by way of non-limiting example. Other arrangements, e.g. a grounded top electrode 120 or both top electrode 120 and bottom electrode 122 floating are of course equally feasible.

The electrodes 120, 122 are typically conductively coupled to a voltage supply 45 arranged to provide the electrode arrangement with a drive voltage having a DC bias component and an AC stimulus component of set frequency in a transmission mode, and with a DC bias voltage in a receive mode, as will be explained in more detail below. The voltage supply 45 may optionally comprise separate stages 102, 104 for providing the DC and AC components respectively, as will be explained in more detail below. The voltage supply 45 may form part of a control module (not shown) to which the ultrasound probe is attached or connected, which control module may supply control signals including the bias voltages and AC stimuli to the ultrasound probe in any suitable manner, such as through a coaxial cable or the like.

The stimulus voltage with set frequency may be applied to the appropriate CMUT cells 100 by a signal amplifier or other suitable voltage supply 45 that generates the drive voltage as a single signal. However, in an alternative embodiment the voltage supply 45 may comprise two stages to generate different components of the drive voltage, i.e. a first stage 102 for generating the static (DC) voltage component and a second stage 104 for generating an alternating voltage component or stimulus having a set alternating frequency, which signal typically is the difference between the overall voltage and the aforementioned static component thereof. Other suitable embodiments of the voltage supply 45 should be apparent, such as for instance an embodiment in which the voltage supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage supply 45 may be implemented in any suitable manner.

Each CMUT cell 100 may be provided with a dedicated DC component and an individual frequency-dependent stimulus, e.g. provided via dedicated drive lines, or at least some of the CMUT cells 100 may be connected to a shared node for providing these CMUT cells 100 with a shared DC component and/or a shared stimulus, and so on. Many suitable configurations will be apparent to the skilled person and it is simply stipulated that any suitable configuration of the voltage supply 45 and its connections to the CMUT cells 100 may be used.

In a preferred embodiment, the static component VDC of the applied drive voltage meets or exceeds the threshold voltage for forcing the CMUT cells 100 into their collapsed states. This has the advantage that the first stage 102 may include relatively large capacitors, e.g. smoothing capacitors, in order to generate a particularly low-noise static component of the overall voltage and prevent crosstalk between the different, e.g. neighboring, CMUT cells 100, which static component typically dominates the overall voltage such that the noise characteristics of the overall voltage signal will be dominated by the noise characteristics of this static component.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

In an embodiment, the bottom electrode 122 is insulated on its cavity-facing surface with an additional layer 125. Suitable electrically insulating layers include an oxide-nitride-oxide (ONO) dielectric layer or an oxide dielectric layer formed from tetraethyl orthosilicate formed above the substrate electrode 122 and below the membrane electrode 120 although it should be understood any electrically insulating material may be contemplated for this layer.

Exemplary techniques for producing the disclosed cavity 118 involve defining the cavity in an initial portion of the membrane layer 114 before adding a top face of the membrane layer 114. As such cavity-forming techniques are well-known per se, they will not be explained in further detail for the sake of brevity only. It should be understood that any suitable cavity-forming technique may be contemplated.

Figure 2:
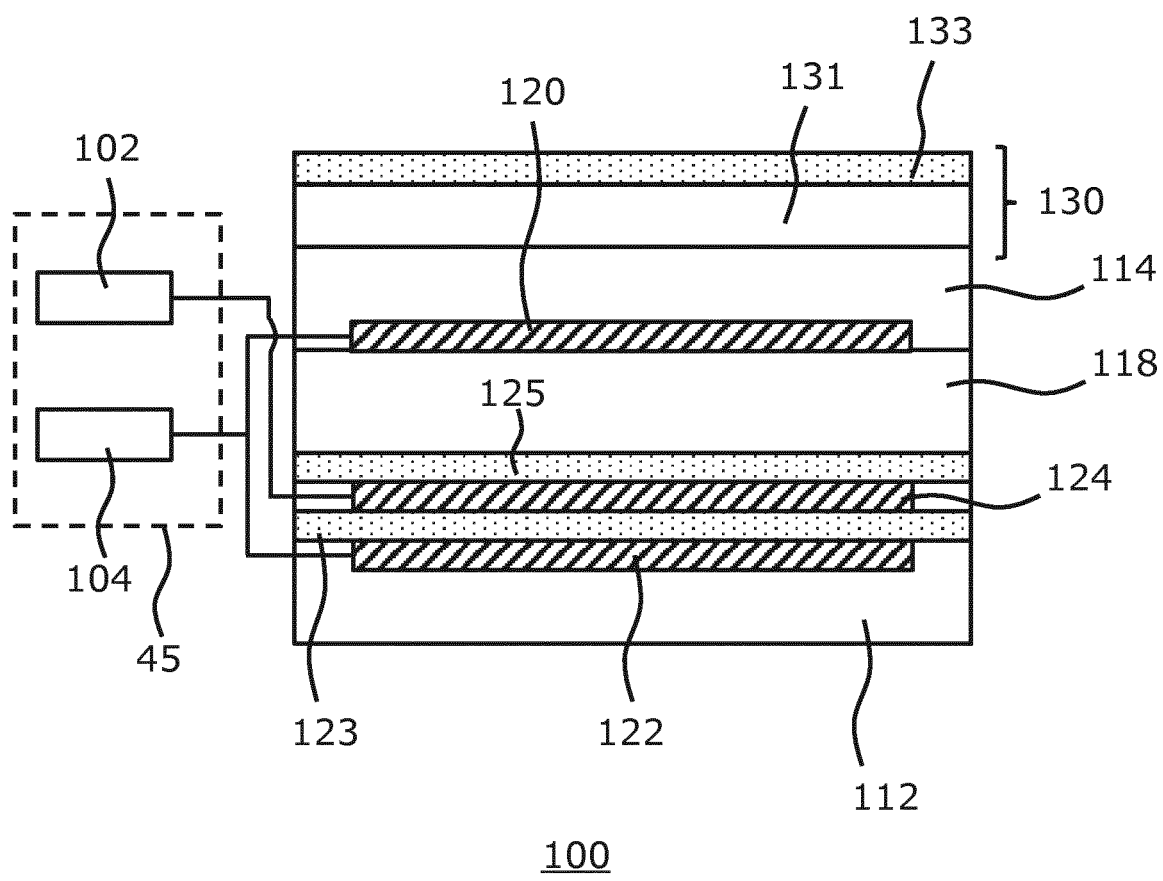
FIG. 2 schematically depicts an aspect of an ultrasound probe according to an alternative embodiment.

An alternative CMUT cell geometry is schematically depicted in FIG. 2, which depicts a 3-electrode CMUT cell 100. This CMUT cell 100 includes a third electrode 124 embedded into the floor of the cell 100 comprising an upper surface of the substrate 112. The bottom electrode 122 may be configured in any suitable manner, e.g. may be circularly configured and embedded into the cell floor 130.

The third electrode 124 is typically insulated on its cavity-facing surface with an upper insulating layer 125 and insulated on its bottom electrode-facing surface with a bottom insulating layer 123. Insulating layers 123 and 125 preferably are silicon dioxide ($SiO_2$) dielectric layers deposited in a TEOS-based deposition process such as a PECVD process. An alternative material for the insulating layers 123, 125 may be oxide-nitride-oxide (ONO), high-k dielectrics and oxides (aluminium oxide, various grades including silane, SiH4-based PECVD SiO$_2$, and so on).

In this embodiment, the first electrode 120 and third electrode 124 of the CMUT cell 100 provide the capacitive plates that develop the actual electrical field across the of the CMUT device, whereas the capacitive coupling between the third electrode 124 and the second electrode 122 through the bottom dielectric layer 123 defines a capacitor, e.g. for a RC filter, which may be integrated in the CMUT cell 100. The first electrode 120 may be brought in vibration by means of a voltage supply 45 adapted to apply an AC stimulus with a set frequency over second electrode 122 and/or first electrode 120, which results in the generation of an acoustic beam, e.g. an acoustic pulse of a particular frequency bandwidth, whereas the third electrode 124 is provided with the DC component of the drive voltage. Third electrode 124 may be connected to a (quasi-) DC voltage by a voltage source, e.g. voltage supply 45, via a large series resistance. As a result, third electrode 124 will "see" the sum of the (quasi-)DC voltage and the RF stimulus provided to electrodes 120, 122. This implementation is particularly attractive in case the CMUT cell 100 has to be stimulated from two sides.

In the exemplary embodiments depicted in FIG. 1 and FIG. 2, the diameter of the cylindrical cavity 118 may be larger than the diameter of the circularly configured electrode plate 122. Electrode 120 may have the same outer diameter as the circularly configured electrode plate 122, although such conformance is not required. Thus, in an exemplary implementation of the present invention, the membrane electrode 120 is fixed relative to the top face of the membrane layer 114 so as to align with the electrode plate 122 below. The electrodes of the CMUT provide the capacitive plates of the device and the gap 118 is the dielectric between the plates of the capacitor. When the diaphragm vibrates, the changing dimension of the dielectric gap between the plates provides a changing capacitance which is sensed as the response of the CMUT to a received acoustic echo.

The spacing between the electrodes is controlled by the application of the DC bias voltage, to the electrodes. As is known per se, by applying a static voltage above a certain threshold, the CMUT cell 100 is forced into a (pre-)collapsed state in which the membrane 114 collapses onto the substrate 112. This threshold value depends on the exact design of the CMUT cell 100 and is defined as the DC bias voltage at which the membrane 114 sticks to (contacts) the cell floor by Vander Waals force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 3a and FIG. 4a.

Figure 3A:
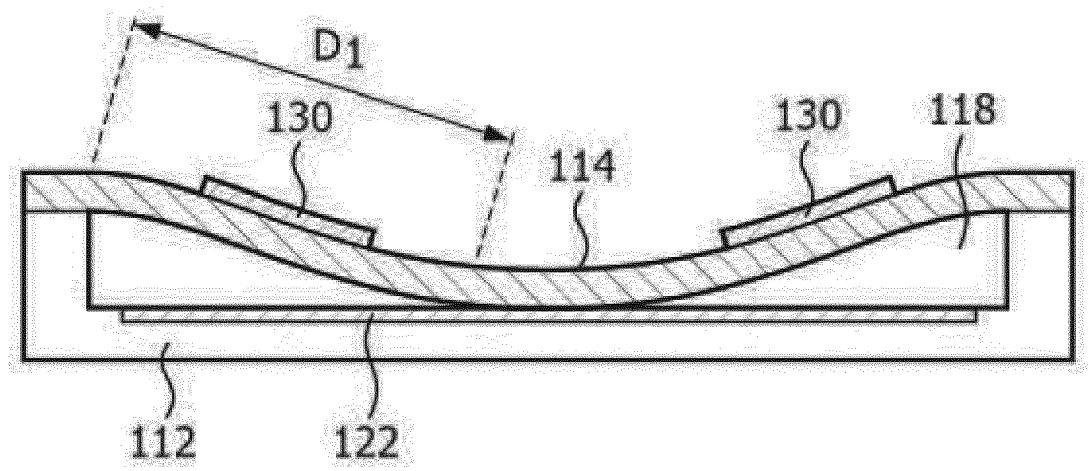
FIGS. 3a, 3b, 4a and 4b schematically depict an operating principle of an aspect of an ultrasound probe according to an embodiment.

The frequency response of a collapse mode CMUT cell 100 may be varied by adjusting the DC bias voltage applied to the CMUT electrodes after collapse. As a result, the resonance frequency of the CMUT cell increases as a higher DC bias voltage is applied to the electrodes. The principles behind this phenomenon are illustrated in FIGS. 3a, 3b, 4a and 4b. The cross-sectional views of FIGS. 3a and 4a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 3a when a relatively low bias voltage is applied, whereas the distance D2 in FIG. 4a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 3a will be lower than the resonant frequency of the CMUT cell in FIG. 4a which is subject to the higher pull-down bias voltage.

Figure 3B:
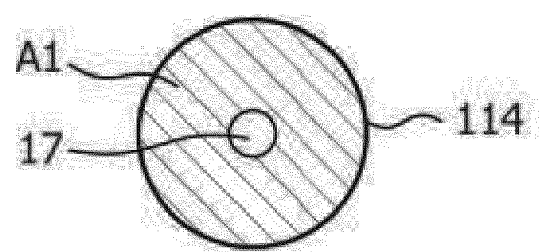
Figure 4A:
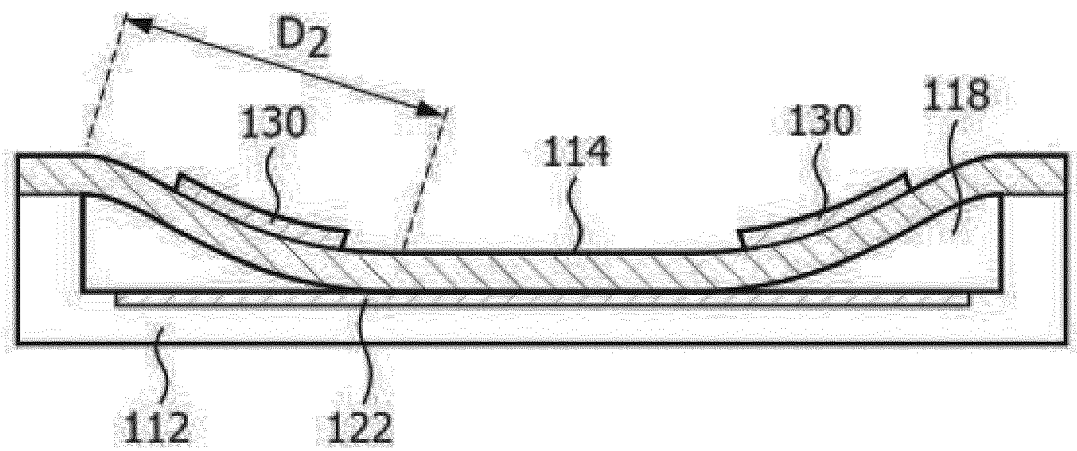
Figure 4B:
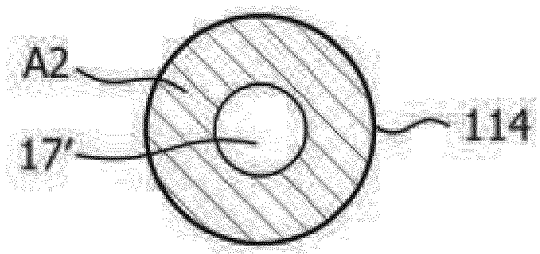

The phenomenon can also be appreciated from the two dimensional illustrations of FIGS. 3b and 4b, as it is in actuality a function of the effective operating area of the CMUT membrane. When the membrane 114 just touches the floor of the CMUT cell as shown in FIG. 3a, the effective vibrating area A1 of the non-contacting (free vibrating) portion of the cell membrane 114 is large as shown in FIG. 3b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage as in FIG. 4a, the greater central contact area 17' results in a smaller free vibrating area A2 as shown in FIG. 4b. This smaller area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

As shown in FIGS. 1 and 2, the CMUT cells 100 are covered by an acoustic window 140, which is typically located in between the CMUT cells 100 and the tissue of the patient during normal use of the ultrasound probe. The acoustic window 140 at least comprises a first layer, typically a first polymer layer, of a polymer having sufficient flexibility to allow movement of the membranes 114 of the CMUT cells 100 and good mechanical robustness to protect the CMUT cells 100 from mechanical damage. Any suitable polymer may be used for this purpose. A particularly suitable example of such a polymer is polydimethylsiloxane (PDMS) although other example polymers include a styrene-ethylene/butylene styrene (SEBS) elastomer, a polybutadiene rubber, a polyurethane, a polymethylpentene such as TPX® as marketed by Mitsui Chemicals America Inc., polybutadiene, polyether block amide (PEBAX) and butyl-rubber. Further examples will be apparent to the skilled person.

A second layer 143 may be present in the acoustic window 140, with the second layer being arranged over the first layer 141 such that during normal use of the ultrasound probe the second layer 143 is arranged in between the tissue of the patient and the first layer 141 (i.e. the first layer 141 is arranged in between the CMUT cells 100 and the second layer 143). Such a second layer 143 for example may be added in case the first layer 141 is not biocompatible and/or is not water-tight. Suitable materials for the second layer 143 for example include parylene and polyether block amide such as polyether block amides available under the trade names PEBAX 2533 and PEBAX 3533. If the second layer 143 has an acoustic impedance different from tissue (typically about 1.6 MRayls) than it should be preferably have a thickness of no more than 10% of the longest wavelength in the bandwidth produced by the CMUT cells 100 in that material. In this way, the acoustic impedance characteristics of the acoustic window 140 are dominated by the first layer 141. Similarly, although the acoustic window 140 in FIGS. 1 and 2 is shown to have two layers, it should be understood that alternative embodiments, e.g. an embodiment in which only the first layer 141 is present or an alternative embodiment in which the acoustic window 140 comprises one or more layers additional to the first layer 141 and the second layer 143 may also be contemplated. It is reiterated that any suitable type of acoustic window 140 may be deployed on the CMUT cells 100.

The one or more layers of the acoustic window 140 may be formed in any suitable manner, as is well-known per se. For example, such layer(s) may be deposited using coating such as inkjetting, spin-coating, dip casting and so on, optionally followed by curing of the layer, e.g. of a curable polymer layer.

Figure 5:
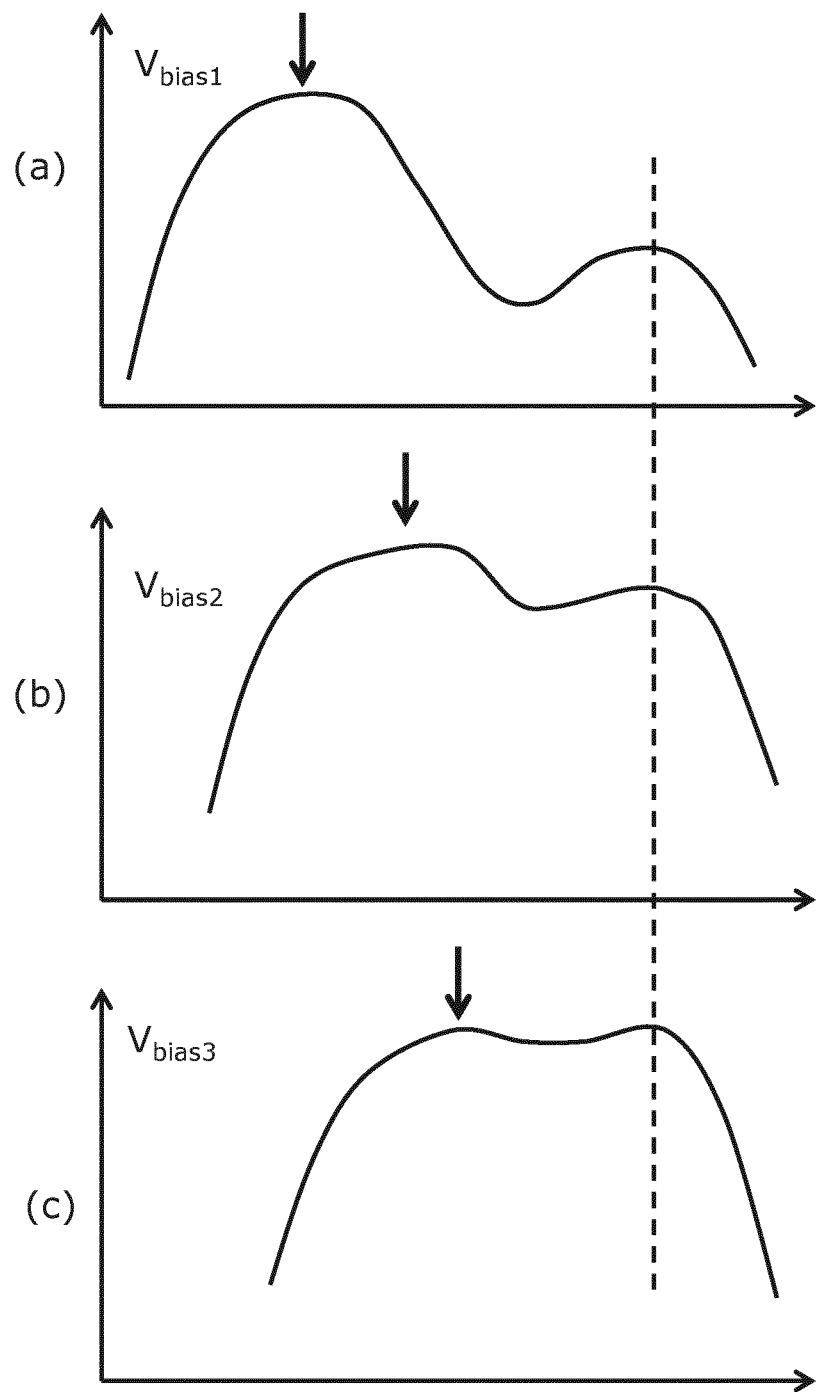
FIG. 5 schematically depicts a typical bias voltage-dependent characteristic of an ultrasound probe having CMUT cells.

FIG. 5 schematically shows a typical frequency response of a CMUT cell 100 operated in collapse mode at (a) bias voltage Vbias1, (b) bias voltage Vbias2 and (c) bias voltage Vbias3, wherein Vbias1<Vbias2<Vbias3. The Y-axes show the intensity of the power spectrum and the X-axes show the frequency distribution of the power spectrum, which power spectrum is the power spectrum of a received pulse echo generated with a short driving pulse. As can be seen in (a)-(c), the power spectra have a bias voltage-dependent component indicated by the arrows and a bias voltage-independent component indicated by the dashed line. The frequency-dependent component is the resonant behavior of the CMUT cell 100, which shifts as a function of the bias voltage applied to the cell, in particular when the CMUT cell 100 is operated in collapse mode, as previously explained. The frequency-independent component results from the acoustic mismatch between the acoustic window material, e.g. PDMS (having an acoustic impedance of about 1 MRayls), and water (having an acoustic impedance of about 1.54 MRayls) being the main constituent of tissue. The center resonance frequency (or peak frequency) of this component occurs at $\lambda/4$ in which $\lambda$ is the principal wavelength of the ultrasound waves in the first layer 141 (PDMS in this example).

Figure 6:
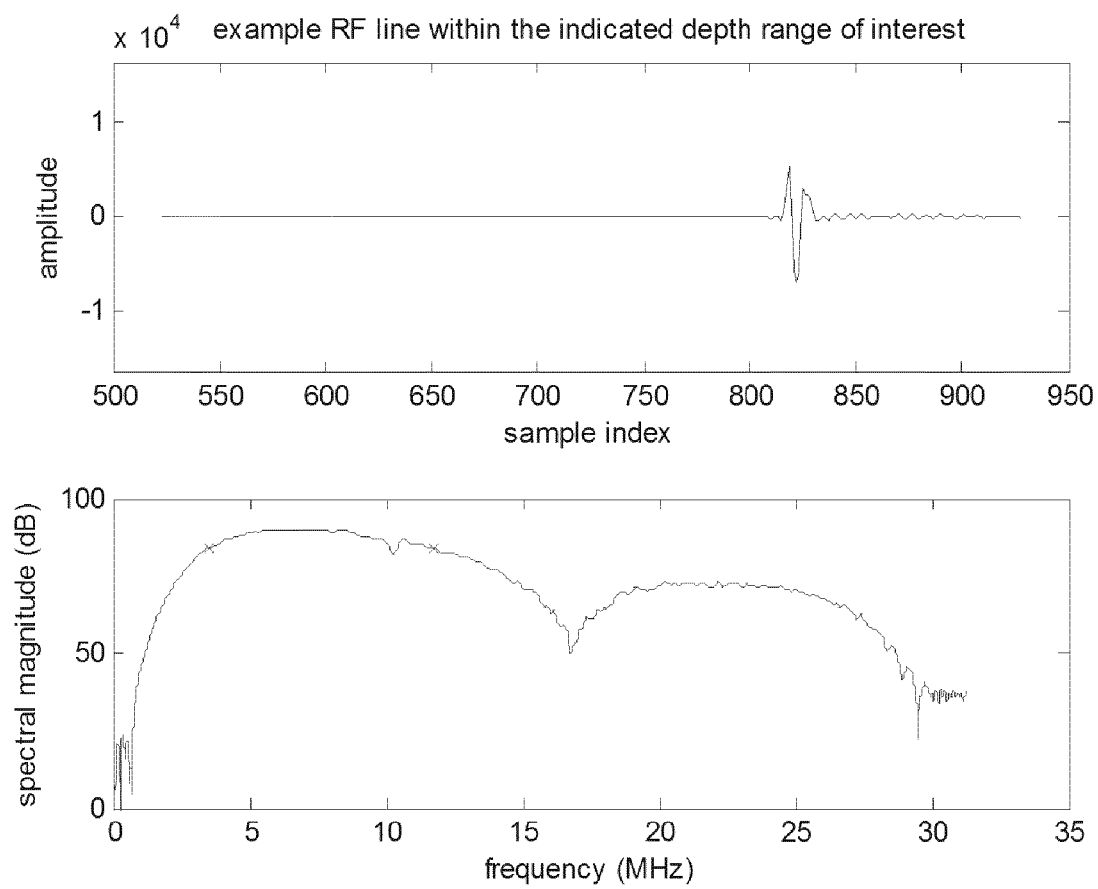
FIG. 6 schematically depicts a power spectrum of an ultrasound probe according to an embodiment.
Figure 7:
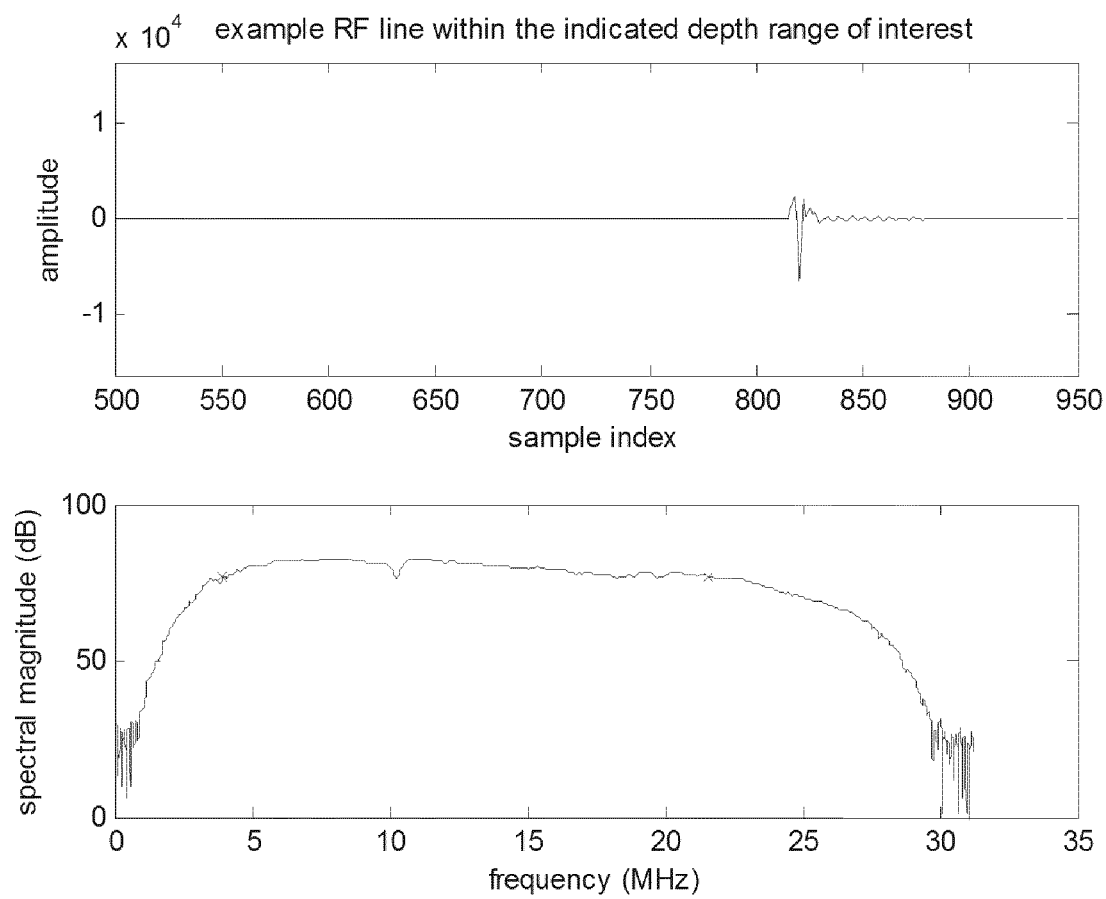
FIG. 7 schematically depicts a further power spectrum of an ultrasound probe according to an embodiment.

What is evident from FIG. 5 is that the effective bandwidth of the power spectrum of the CMUT cell 100 may be increased by matching the center resonance frequency of the cell to the center resonance frequency of the acoustic window 140. This is further evident from FIGS. 6 and 7, which depict the power spectrum of a CMUT device having 32 CMUT cells each having membrane with a diameter of 60 µm such that the CMUT cell is optimized to operate with a center frequency range of about 7-11 MHz and a PDMS acoustic window having a thickness of about 11 µm. Consequently the first order resonance frequency due to acoustic mismatch of the acoustic window to water occurs at 22.7 MHz (assuming that speed of sound in water is 1000 m/s). In FIG. 6, the CMUT cells are biased by a bias voltage of −100V yielding an effective bandwidth of 8.16 MHz and center frequency 7.6 MHz (93% bandwidth) whereas in FIG. 7, the CMUT cells are biased by a bias voltage of −150V yielding an effective bandwidth of 17.65 MHz and center frequency 12.8 MHz (138% bandwidth). From the above, it may be concluded that it is desirable to operate the CMUT cells 100 at a fixed bias voltage at which the effective bandwidth of the CMUT cells 100 is optimized by superimposing the frequency response of the CMUT cells 100 onto the resonance frequency of the acoustic window 140, e.g. by aligning the center resonance frequency of the CMUT cells 100 with the (bias voltage-independent) first order center resonance frequency of the acoustic window 140 or at least shifting the center resonance frequency of the CMUT cells 100 towards the first order center resonance frequency of the acoustic window 140 such that the region of the composite resonance spectrum delimited by this center or peak resonance frequency of the CMUT cells 100 and the first order resonance frequency (peak) of the acoustic window 140 exhibits a minimum resonance strength no more than 6 dB, preferably no more than 3 dB, below the maximal resonance strength of the composite resonance spectrum, thereby avoiding a significant dip in the strength of the composite resonance spectrum in between the peak resonance frequency of the CMUT cells 100 and the first order resonance frequency of the acoustic window 140, which effectively increases the bandwidth of the power spectrum.

As will be well-known to the skilled person, the effective bandwidth of an ultrasound probe, e.g. an array of CMUT cells 100, is typically determined on the basis of the spectral composition of a received pulse echo, which pulse echo may be obtained in any suitable manner, e.g. by positioning of the ultrasound probe on a suitable body portion, e.g adjacent to an anatomic site of interest, and transmitting an ultrasound pulse or beam into the suitable body portion with the ultrasound probe. The effective bandwidth is sometimes referred to as the −6 dB bandwidth, i.e. the continuous part of the echo spectrum in which the difference between maximum strength and minimum strength does not exceed 6 dB. In other words, where reference is made to effective bandwidth in the present application, this may refer to the effective bandwidth of the ultrasound pulses travelling through mammalian, e.g human, tissue.

At this point, it is noted that the frequency response of the acoustic window 140, e.g. the first layer 141 is a function of the magnitude of the acoustic impedance mismatch between the acoustic window 140 and the tissue to be imaged. The FWHM of the frequency response typically decreases and the maximum intensity increases with an increasing magnitude of this mismatch. This behaviour may be utilized in tuning the effective bandwidth of the CMUT cells 100 by manipulating the acoustic impedance mismatch between the acoustic window 140 and the tissue to be imaged. This for example may be achieved by distributing a particulate material through the first (polymer) layer, e.g. metal particles, metal oxide particles, ceramic particles, or the like, for tuning the impedance of the first layer 141, as is well-known per se. By controlling the type and amount of particles to be distributed through the first layer 141, the shape of the frequency response of the acoustic window 140 may be controlled, for example to extend the effective bandwidth of the CMUT cells 100 as explained above.

As will be understood from the foregoing, an ultrasound probe comprising a transducer array of CMUT cells 100 has a set of operating parameters including bias voltage at which the effective bandwidth of the CMUT cells 100 is operated, thereby minimizing the interference resulting from the acoustic window 140. This may be operation in any mode of the CMUT cells 100, although preferably the CMUT cells 100 are operated in pre-collapse mode or collapse mode. However, for a batch of such ultrasound probes, the optimal operating parameters for each probe may be different, as they depend on variations within manufacturing tolerances, e.g. variations in thickness of the acoustic window layer(s) and the thickness of the membranes 114 of the CMUT cells 100. Consequently, it is not possible to provide a single set of operating instructions (i.e. specified operating parameters) for the batch that would lead to each probe of the batch being operated at its most effective bandwidth. However, as previously explained, it is not desirable for the end user to have to determine these operating conditions at the point of care.

Figure 8:
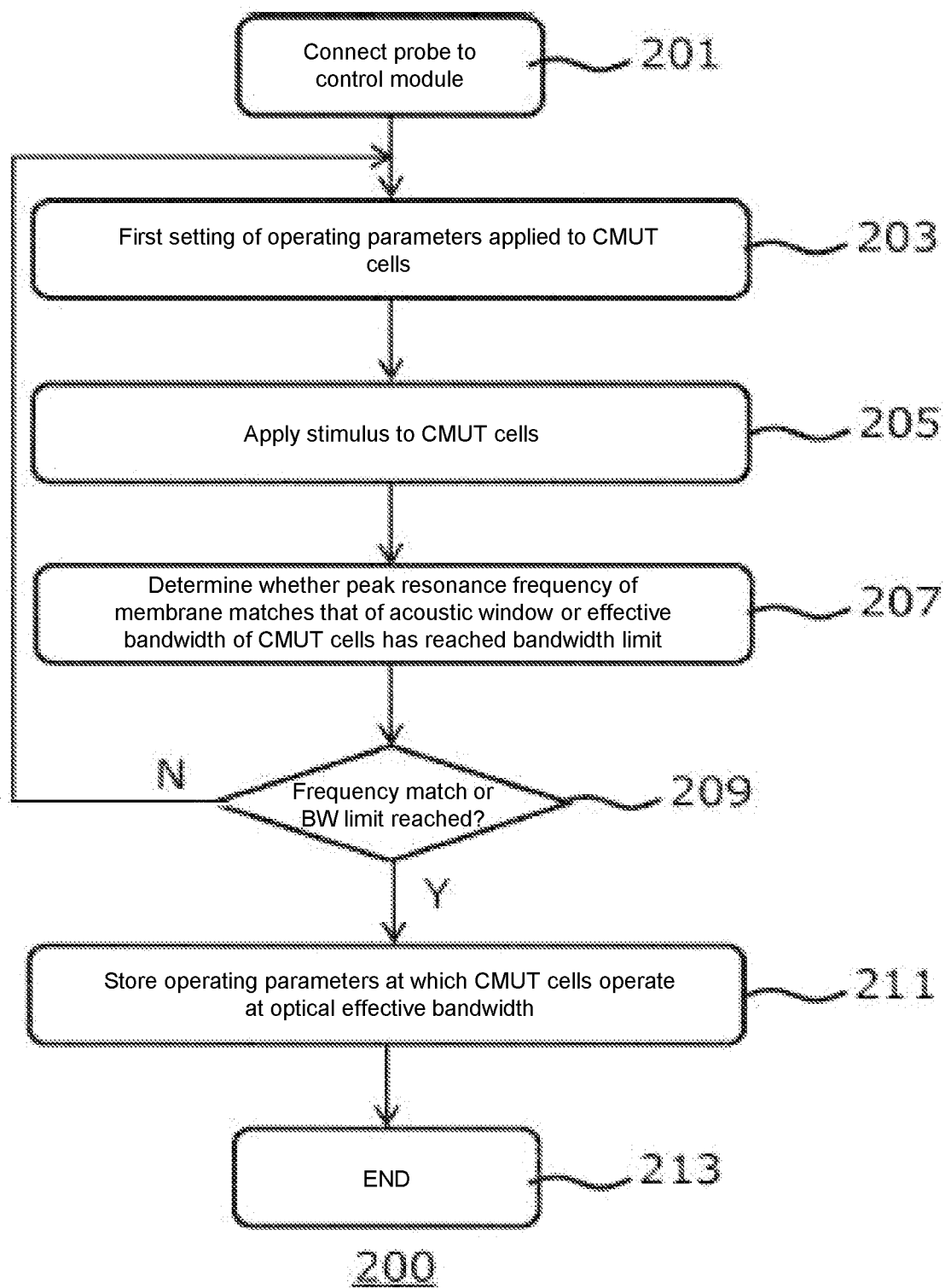
FIG. 8 is a flowchart of a method of calibrating an ultrasound probe according to an embodiment.

In accordance with an aspect of the present invention, this has been addressed by a calibration method 200, a flowchart of which is depicted in FIG. 8, which calibration method is applied to an ultrasound probe comprising an ultrasound transducer array including CMUT cells 100 covered by an acoustic window 140, for example each ultrasound probe of a batch of such ultrasound probes. The calibration method 200 has the purpose of determining the optimal effective bandwidth of the ultrasound probe by systematically varying operating parameters, in particular bias voltage. Such an optimal effective bandwidth for instance may be achieved if the bias voltage-dependent peak resonance frequency of the CMUT cells 100 matches the bias voltage-independent peak resonance frequency of the acoustic window 140 and the full bandwidth (power spectrum) of the CMUT cells 100 lies within a target operational bandwidth of the transducer array. Alternatively, such an optimal effective bandwidth may be the maximum possible bandwidth within the target operational bandwidth of the transducer array. In this scenario, the bias voltage-dependent peak resonance frequency of the CMUT cells 100 may not match the bias voltage-independent peak resonance frequency of the acoustic window 140; instead, in this scenario a difference between the bias voltage-dependent peak resonance frequency of the CMUT cells 100 and the bias voltage-independent peak resonance frequency of the acoustic window 140 may be minimized.

The calibration method 200 starts in 201, for example by connecting the ultrasound probe to control module including the voltage supply 45, after which the method proceeds to 203 in which a first set of operating parameters, e.g. a first bias voltage, is applied to the CMUT cells 100 of the probe, for example to drive the CMUT cells 100 into a first state of collapse or pre-collapse. The first set of operating parameters for example may be chosen based on the intended design values of for example membrane thickness, membrane diameter and acoustic window thickness, to name but a few. Subsequently, in 205 a stimulus is applied to the CMUT cells 100, which stimulus typically defines a short pulse, and the pulse echoes of this pulse are collected with the CMUT cells 100. As previously explained, the response collected with the CMUT cells 100 typically includes a bias voltage-dependent component corresponding to the resonance frequency of the CMUT cells 100, which is a function of the bias voltage applied to the CMUT cells 100, i.e. the area of the membrane 114 of the CMUT cells 100 collapsed onto the substrate 112, as well as a bias voltage-independent component originating from the resonance of the acoustic window 140. However, it should be understood that this calibration method equally may be applied to CMUT cells to be operated in pre-collapse or non-collapsed modes.

In 207, it is checked if the peak resonance frequency of the membrane 114 matches that of the acoustic window 140 or if the effective bandwidth of the CMUT cells 100 has reached a limit of the operational bandwidth of the transducer array. If neither is the case, as checked in 209, the method 200 reverts back to 203 in which the operating parameters, most notably the bias voltage, of the CMUT cells 100 are adjusted, e.g. in a systematic manner, after which the previously described steps are repeated until the peak resonance frequency of the membrane 114 matches that of the acoustic window 140 or if the effective bandwidth of the CMUT cells 100 has reached a limit of the operational bandwidth of the transducer array, such that the CMUT cells 100 operate at their optimal effective bandwidth, e.g such that the center resonance frequency of the CMUT cells 100 is shifted towards the first order center resonance frequency of the acoustic window 140 such that the region of the overall resonance spectrum delimited by this center or peak resonance frequency of the CMUT cells 100 and the first order resonance frequency of the acoustic window 140 exhibits a minimum strength no more than 6 dB below the maximum strength in the composite resonance spectrum, and preferably has a minimum strength of at least 10 dB. Once it has been decided in 209 that the CMUT cells 100 operate at optimal effective bandwidth, the calibration method 200 proceeds to 211 in which the operating parameters at which the CMUT cells 100 operate at their optimal effective bandwidth are stored in a data storage device of the ultrasound probe as will be explained in more detail below. The stored operating parameters include the bias voltage and optionally further include additional operating parameters such as effective bandwidth, peak resonance frequency and transmit/receive sensitivity of the transducer array. Upon storage of the operating parameters in the data storage element 150 of the ultrasound probe, the calibration method 200 terminates in 213.

At this point, it should be noted that the CMUT cells 100 of the probe are not necessarily all identical. It is for instance equally feasible that the probe contains different types of CMUT cells 100, e.g. cells having a different membrane thickness, material and/or diameter, in which case the data storage element 150 may contain multiple sets of configuration parameters, with each set corresponding to a particular type of CMUT cells 100 of the probe. Similarly, not all CMUT cells are necessarily addressed in the same manner. For example, in so-called 1.5D transducers different bias voltages may be applied to different regions of the probe. Hence, it should be understood that embodiments of the present invention are not limited to the provision and storage of a single set of configuration parameters that apply to all CMUT cells 100 of the probe.

Figure 9:
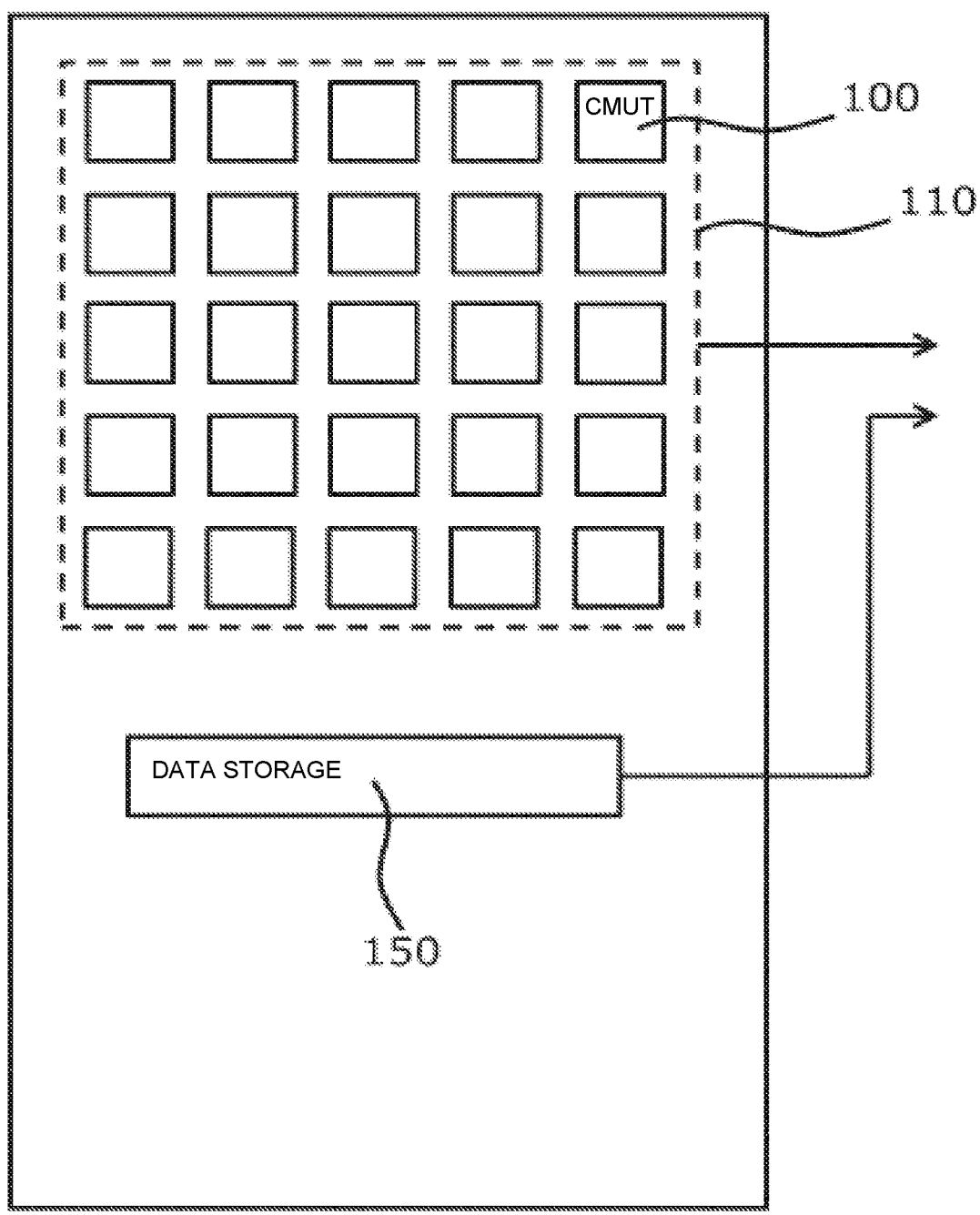
FIG. 9 schematically depicts an ultrasound probe according to an embodiment.

FIG. 9 schematically depicts an ultrasound probe 10 according to an example embodiment. The ultrasound probe 10 comprises a transducer array 110 comprising a plurality of CMUT cells 100, which sells may be arranged in any suitable arrangement, e.g. a one-dimensional array, a two-dimensional array, etcetera. As previously explained, the particular implementation of the transducer array 110 and the CMUT cells 100 is not particularly limited and it should be understood that any suitable type of transducer array 110 and CMUT cells 100 may be deployed in such an ultrasound probe 10. Similarly, the transducer array 110 may be operated in any suitable manner; for example, each CMUT cell 100 may be individually addressed or alternatively the transducer array 110 may comprise clusters of CMUT cells 100 that are addressed in unison.

In accordance with an aspect of the present invention, the ultrasound probe 10 further comprises a data storage element 150 in which the operational parameters as generated with the calibration method 200 as described above are stored. Such a data storage element 150 may be a data storage element that can be optically read, e.g. a barcode, QR code or the like, or preferably may be a data storage device that can be electronically read, e.g. a memory or the like. Such a data storage device preferably is a data storage device that can retain data in the absence of a permanent power supply. A particular suitable example of such a data storage device 150 is an EEPROM, although other types of ROM may also be contemplated, as may other suitable types of memory, e.g. a Flash memory or the like. As will be understood by the skilled person, the use of a ROM has the advantage that the operational parameters stored in the device cannot be accidentally overwritten.

In case of an optical data storage element 150, this may further involve contacting a database, e.g. over a network such as the Internet, to retrieve the configuration information from said database in case the optical data storage element 150 contains a reference code or identifier based on which the desired configuration information can be retrieved from the database. Alternatively, the configuration information may be self-contained by the optical data storage element 150.

Figure 10:
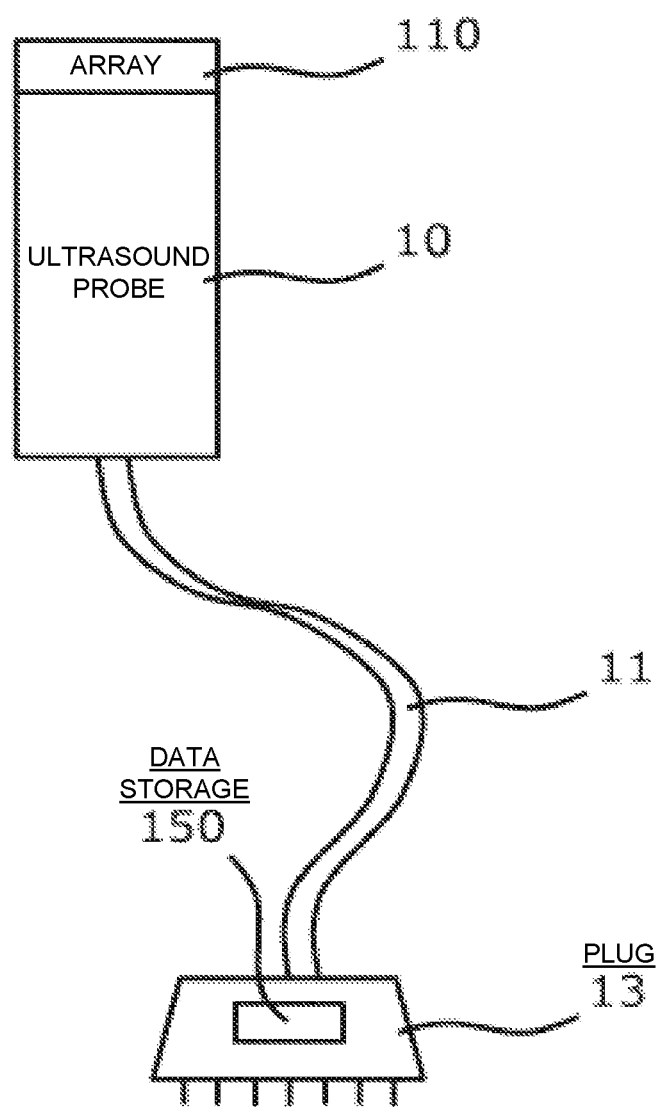
FIG. 10 schematically depicts an ultrasound probe according to another embodiment.

In FIG. 9, the data storage element 150, here a data storage device, is shown within the housing of the ultrasound probe 10. This for example is feasible in embodiments where the ultrasound probe 10 is relatively large, such that the probe contains sufficient space for housing the data storage element 150. This for example is the case if the ultrasound probe 10 is a handheld probe used for diagnostic imaging purposes by placing the probe on a part of the body of a patient. However, certain application domains of such ultrasound probes, e.g. ultrasound probes used in interventional procedures, requires that the ultrasound probe 10 is as compact as possible, for example if the ultrasound probe 10 forms part of an interventional device such as a catheter or the like, in which case it may not be desirable to include the data storage element 150 within the housing or body of the ultrasound probe 10. For this reason, in an alternative embodiment as schematically depicted in FIG. 10, the data storage element 150 may be included in a plug 13 for connecting the ultrasound probe 10 (e.g. as part of a catheter or the like) to the control module, which plug 13 may be connected to the ultrasound probe 10 in any suitable manner, e.g. at least in part through a cable 11 such as a coaxial cable or the like. Such plugs and connection arrangements are well-known per se and are therefore not further discussed for the sake of brevity only, it should be understood that any suitable plug and connection arrangement for connecting the plug 13 to the ultrasound probe 10 may be contemplated.

For the avoidance of doubt, it is noted that where the data storage element 150 is to be optically read, the data storage element 150 may be positioned in a visible location on the ultrasound probe 10, e.g. as a sticker or the like attached to an external surface of the ultrasound probe 10.

Figure 11:
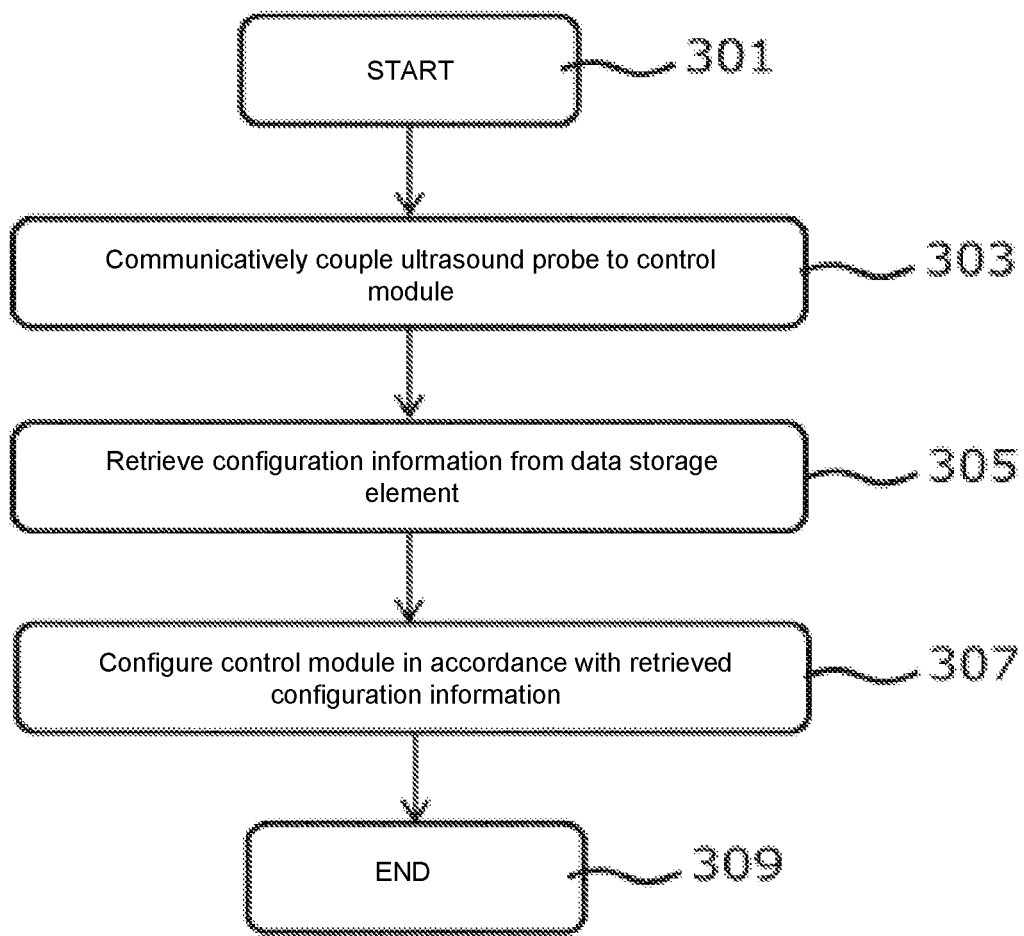
FIG. 11 is a flowchart of a method of operating an ultrasound system according to an embodiment' and FIG. 12 schematically depicts an ultrasound system according to an example embodiment.

The control module of the ultrasound probe 10 may take any suitable form. For example, the control module may be a dedicated unit such as a console or the like or alternatively may be a computer programmed to act as the control module for the ultrasound probe 10. The ultrasound probe 10 and a control module may form part of an ultrasound or monitoring system such as an ultrasound diagnostic imaging system; an interventional system including ultrasound imaging facilities provided by one or more ultrasound probes 10 or a patient care monitoring system arranged to process ultrasound data provided by an ultrasound probes for vital signs extractions. In the case of monitoring system the ultrasound data are preferably collected by the low profile ultrasound probe or a patch, which might be more comfortable for the long period monitoring. The control module is typically arranged to retrieve the configuration information from the data storage element 150 and to operate the transducer array 110, i.e. the CMUT cells 100, in accordance with the retrieved configuration information. This for example may be achieved in accordance with the method 300 of operating an ultrasound system including the ultrasound probe 10 and such a control module, a flowchart of which is depicted in FIG. 11. The method 300 commences in 301 and proceeds to 303 in which the ultrasound probe 10 is communicatively coupled to the control module, e.g. by inserting the block 13 into a matching socket of the control module. Subsequently, the control module retrieves the configuration information, i.e. the operating parameters, for the transducer array 110 from the data storage element 150. This may be done automatically in response to the control module detecting the connection with the ultrasound probe 10, or alternatively may be triggered by the user of the control module providing a command, e.g. using a user interface, triggering the control module to retrieve the configuration information from the data storage element 150. As explained above, such retrieval may be performed electronically in case the data storage element 150 is a memory or the like, or optically using an optical reader such as a scanner in case the data storage element 150 is optically readable code such as a barcode, QR code or the like.

In 307, the control module configures itself in accordance with the retrieved configuration information such that the ultrasound probe 10 is operated in accordance with the retrieved configuration information, such as the retrieved bias voltage at which the respective one or more sets of CMUT cells 100 are to be operated to ensure that the respective CMUT cells 100 operate at their optimal bandwidth as previously explained. Upon completing such a configuration, the method 300 terminates in 309.

At this point, it is noted that the configuration information retrieved from the data storage element 150 may further comprise operating characteristics of the ultrasound probe 10, such as optimal bandwidth, peak resonance frequencies, and so on for the one or more sets of CMUT cells 100 as previously explained. These operating characteristics may be used to verify whether the ultrasound probe 10 still operates as intended, thereby allowing a user to alter the configuration information, i.e. operating parameters of the ultrasound probe 10, upon determining that the actual operating characteristics of the ultrasound probe 10 no longer correspond to its intended operating characteristics. Such a deviation from the intended operating characteristics for example may be caused by ageing of the CMUT cells 100 or the acoustic window 140, by damage to the transducer array 110, and so on.

Figure 12:
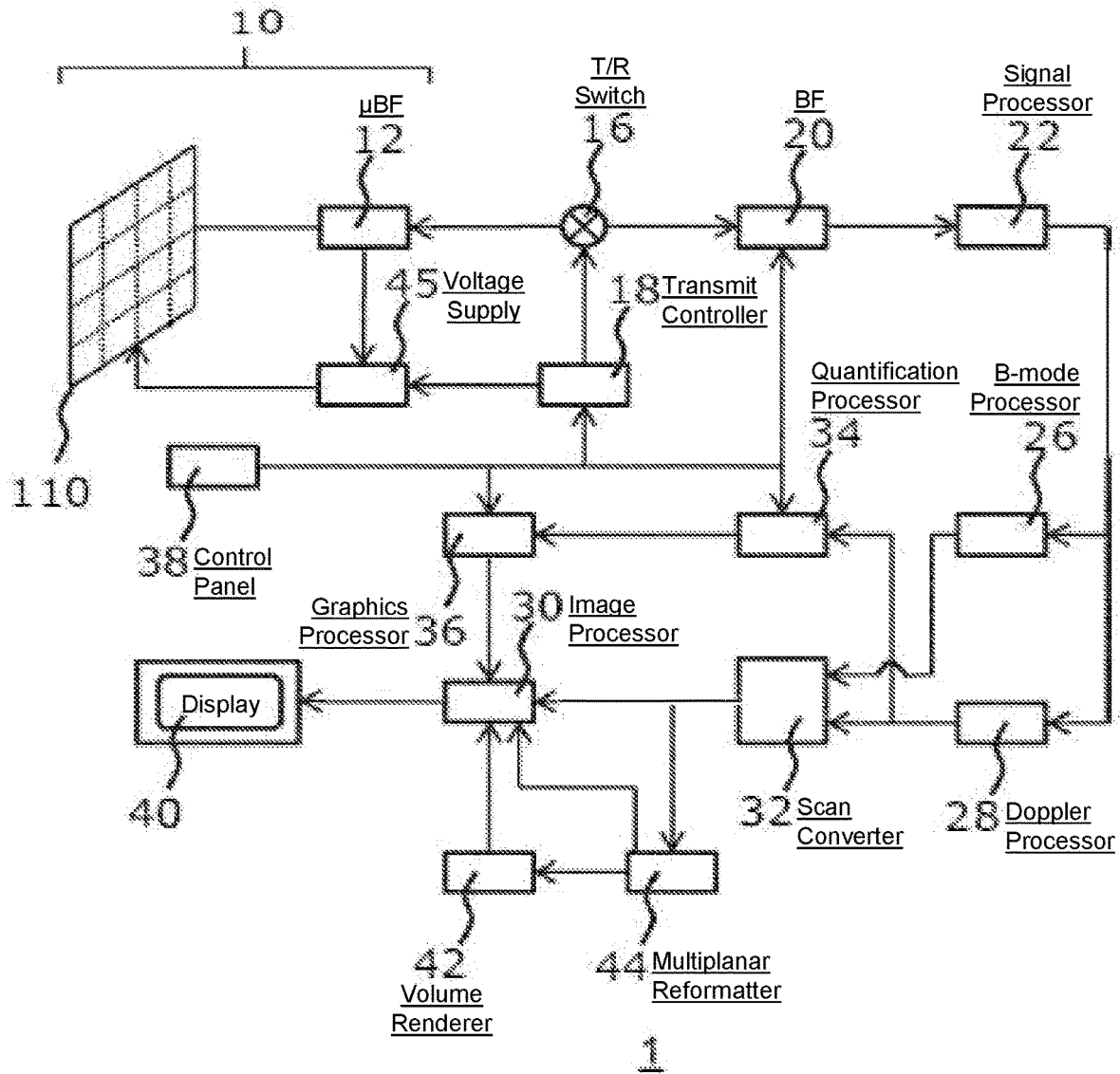

FIG. 12 schematically depicts an example embodiment of an ultrasonic diagnostic imaging system in block diagram form. In FIG. 12, a CMUT transducer array 110 is provided in an ultrasound probe 10 for transmitting ultrasonic waves and receiving echo information. The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells, in particular controls the delays and apodication of these signals. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable 11, e.g. coaxial wire, to a control module. The control module includes a transmit/receive (T/R) switch 16 which switches between transmission and reception modes and protects the main beam former 20 of the control module from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control the voltage supply 45 for the CMUT array. For instance, the voltage supply 45 sets the various DC and AC bias voltage(s) that are applied to the CMUT cells 100 of a CMUT array 110, e.g. to generate the narrowband pulses of different frequency in the respective transmission modes and to set the resonance frequencies of the CMUT cells 100 in the respective receive modes as explained above.

The partially beam-formed signals produced by the microbeam former 12 are forwarded to the main beam former 20 where partially beam-formed signals from individual patches of transducer elements are combined into a fully beam-formed signal and digitized. For example, the main beam former 20 may have 128 channels, each of which receives a partially beam-formed signal from a patch of dozens or hundreds of CMUT transducer cells 100. In this way the signals received by thousands of transducer elements of a transducer array 110 can contribute efficiently to a single beam-formed signal.

At this point it is noted that it is of course well-known per se that the microbeam former 12 may be omitted, for instance when there is no need to reduce the number of signals to be provided from the probe 10 to the beam former 20 of the control module. Microbeam formers are typically present where such a need does exists, e.g. in some 1-D and 2-D imaging architectures.

The beam-formed signals are coupled to a signal processor 22. The signal processor 22 can process the received echo signals in various ways, such as bandpass filtering, decimation, I and Q component separation, e.g. after IF mixing/demodulation, for envelop detection, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of calibrating an ultrasound probe, comprising:
   systematically varying a bias voltage of an array of capacitive micromachined ultrasound transducer (CMUT) cells of the ultrasound probe to a plurality of voltages associated with a collapse mode of the array of CMUT cells, wherein the ultrasound probe comprises:
      the array of CMUT cells, each cell comprising a substrate carrying a first electrode of an electrode arrangement, the substrate being at least partially spatially separated from a flexible membrane including a second electrode of the electrode arrangement by a gap, wherein a configurable area of the flexible membrane is collapsed onto the substrate in the collapse mode;
      an acoustic window over the array of CMUT cells; and
      a data storage element accessible to an external control module in communication with the ultrasound probe;
   for each respective voltage of the plurality of voltages, determining a composite resonance spectrum of the ultrasound probe resulting from operation of the array of CMUT cells at the respective voltage, the composite resonance spectrum comprising:
      a first order resonance frequency of the acoustic window; and
      a resonance spectrum of the array of CMUT cells, wherein the resonance spectrum and the first order resonance frequency at least partially overlap;
   determining a selected bias voltage from among the plurality of voltages based on the composite resonance spectrum; and
   storing the selected bias voltage in the data storage element.

2. The method of claim 1, further comprising storing an effective bandwidth of the array of CMUT cells achieved with the selected bias voltage in the data storage element.

3. The method of claim 1, further comprising:
   retrieving, using the external control module, the selected bias voltage from the data storage element; and
   operating, using the external control module, the array of CMUT cells in accordance with the selected bias voltage.

4. An ultrasound probe comprising:
   an array of capacitive micromachined ultrasound transducer (CMUT) cells, each cell comprising a substrate carrying a first electrode of an electrode arrangement, the substrate being at least partially spatially separated from a flexible membrane including a second electrode of the electrode arrangement by a gap, wherein a configurable area of the flexible membrane is collapsed onto the substrate in a collapse mode of the array of CMUT cells;
   an acoustic window disposed over the array of CMUT cells; and
   a data storage element accessible to an external control module in communication with the ultrasound probe,
   wherein a bias voltage of the array of CMUT cells is configured to be systematically varied to a plurality of voltages associated with the collapse mode,
   wherein each respective voltage of the plurality of voltages is associated with a composite resonance spectrum of the ultrasound probe resulting from operation of the array of CMUT cells at the respective voltage, the composite resonance spectrum comprising:
      a first order resonance frequency of the acoustic window; and
      a resonance spectrum of the array of CMUT cells, wherein the resonance spectrum and the first order resonance frequency at least partially overlap, and
   wherein the data storage element is configured to store a selected bias voltage determined from among the plurality of voltages based on the composite resonance spectrum.

5. The ultrasound probe of claim 4, wherein the data storage element comprises a memory.

6. The ultrasound probe of claim 4, further comprising a cable including a plug for connecting the ultrasound probe to the external control module, wherein the data storage element is located in the plug.

7. The ultrasound probe of claim 4, wherein the acoustic window comprises a first polymer layer contacting the array of CMUT cells.

8. The ultrasound probe of claim 7, wherein the first polymer layer comprises polydimethylsiloxane (PDMS).

9. The ultrasound probe of claim 7, wherein the acoustic window further comprises a second polymer layer over the first polymer layer.

10. The ultrasound probe of claim 9, wherein the second polymer layer comprises a polyether block amide or parylene.

11. The ultrasound probe of claim 7, wherein the first polymer layer further includes a filler material.

12. The ultrasound probe of claim 4, wherein the ultrasound probe is a low profile ultrasound probe suitable for long term monitoring.

13. An ultrasound system, comprising:
   the ultrasound probe of claim 4; and
   the external control module, wherein the external control module is adapted to:
      retrieve the selected bias voltage from the data storage element; and
      operate the array of CMUT cells in accordance with the selected bias voltage.

14. The ultrasound probe of claim 4, wherein the data storage element is further configured to store an effective bandwidth of the array of CMUT cells achieved with the selected bias voltage.

15. The ultrasound probe of claim 4,
   wherein the resonance spectrum comprises a peak resonance frequency,
   wherein the selected bias voltage is configured to cause at least one of:
      a region of the composite resonance spectrum to exhibit a minimum resonance strength no more than 6 dB below a maximum resonance strength of the composite resonance spectrum, wherein the region is delimited by the peak resonance frequency and the first order resonance frequency; or the peak resonance frequency to coincide with the first order resonance frequency.

* * * * *